Nov. 1, 1955 T. E. MOTOSE Plant Pat. 1,428
ROSE PLANT
Filed Jan. 11, 1955
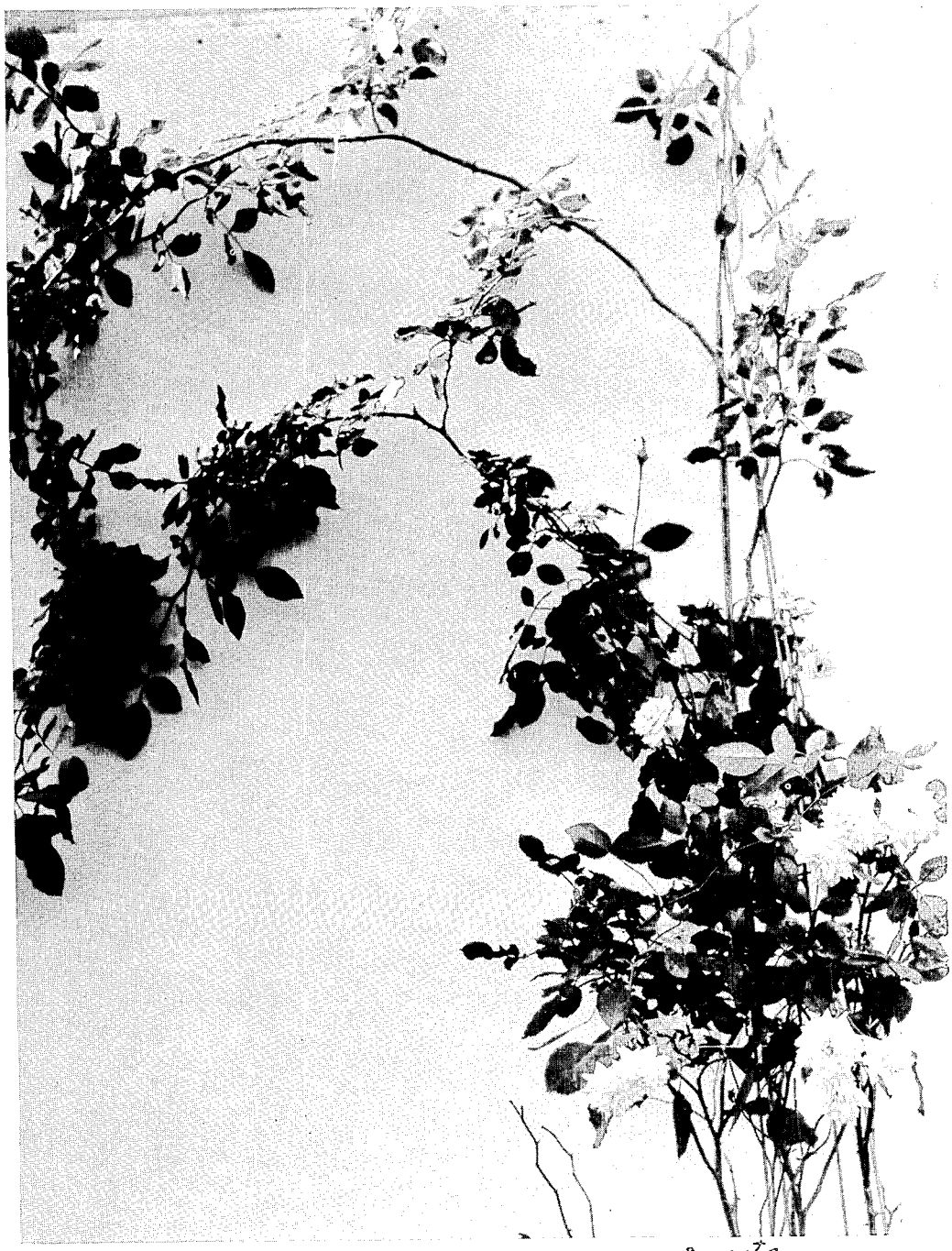
Inventor
Thomas Edison Motose United States Patent Office Plant Pat. 1,428
Patented Nov. 1, 1955

1,428

ROSE PLANT

Thomas Edison Motose, Fairport, N. Y.

Application January 11, 1955, Serial No. 481,288

1 Claim. (Cl. 47—61)

This discovery or invention relates to a new and distinct variety of climbing rose plant originating as a mutation of the bush variety known in commerce as Demure (Plant Patent No. 1,065).

Demure, the parent variety of this discovery, is a low-growing bush of the floribunda class, reaching a height of about one and one-half feet, and occasionally two and one-half feet, when fully grown outdoors, and has the usual recurrent blooming habit of similar class of roses. It bears cameo-pink flowers (about two and one-half inches in diameter when fully opened and forty or more petals to an average bloom), which are borne in clusters and sometimes singly.

The climbing sport or mutation, the subject of the present application, was found by me on said Demure bush, owned and grown personally by me. I am the sole owner of both the parent bush and the climbing sport.

The leaves, buds, bark, thorns, colors, fragrance and blooming habit of the new variety are the same as those of its parent, but the new variety is distinguished from its parent by the long shoots or climbing canes that attain a height of ten to fifteen feet when mature.

Asexual reproductions of the said new variety by the usual methods of budding, grafting and cutting, performed in Fairport, N. Y., show that the climbing and other characteristics described in the immediately preceding paragraph and in the detailed specification that follows come true to form and are fully established and transmitted through succeeding propagations.

The accompanying picture of the new variety shows its climbing characteristic, canes, foliage and blooms. Since the colors of the various parts of the new variety are the same as those of similar parts of the parent variety, and color is not the distinguishing characteristic between the said two varieties, the accompanying picture is not colored.

Observations of the new variety for the specific purpose of compiling data for this application were made on sunny days in the month of August 1954, on a plant almost 14 feet tall growing outdoors in Fairport, N. Y.

The color terminology used in describing the new variety is in accordance with Ridgway's Color Standard and Nomenclature (whenever plate number is given) and general dictionary meaning (when plate number is not given).

The following is a detailed description of the new variety:

(*a*) Parentage: A sport (mutant) of Demure.

(*b*) Classification: Climbing hybrid polyantha rose (botanic). Climbing floribunda (commercial).

(*c*) Blooming habit: Recurrent—continuous.

(*d*) Flowering bud:

*Size.*—Small.

*Shape.*—Ovoid.

*Color when sepals begin to divide.*—Rose Pink (Plate 12).

*Color when half blown.*—Cameo Pink (Plate 26), with White (Plate 53) overcast at the base of visible petals.

*Sepals.*—Well serrated with tendency to curl back when petals unfurl, Biscay Green (Plate 17) inside and Bice Green (Plate 17) outside.

*Calyx.*—Small, smooth and Biscay Green (Plate 17).

*Peduncle.*—Small, short, slender, slightly rough and Biscay Green (Plate 17).

*Opening characteristic.*—Opens up very well and not affected by normal weather condition found during growing seasons in Fairport, N. Y.

(*e*) Flower:

*Size when fully opened.*—Two to two and one-half inches in diameter.

*Quantity to a stem or flowering branch.*—One, sometimes three or four.

*Form.*—Cupped (when partly opened); flattens out slightly when fully blown.

*Petalage.*—Double, normally exceeds 40 in number, and rarely falls below that quantity.

*Fragrance.*—Average hybrid-tea fragrance, tea-scented.

*Lasting quality.*—Very long, a week or more.

*Color.*—Cameo Pink (Plate 26) inner petals or those near the center; White (Plate 53) lightly overcast with Cameo Pink (Plate 26) outer petals; cream, and often light yellow, base.

*Discoloration.*—General tonality at the end of four or five days is still Cameo Pink in good weather, and becoming slightly lighter, but still retaining the basic pink shade, towards the end of seven days; creamy or creamy pink in over-all coloring a few days before the petals fall.

(*f*) Average petal:

*Appearance.*—Satiny inside and shiny outside.

*Form.*—Oval.

*Arrangements.*—Irregular.

*Color.*—Inner petals Cameo Pink (Plate 26), with little or no difference between their obverse and reverse sides; outer petals White (Plate 53) slightly overcast with Cameo Pink (Plate 26), with little or no difference between their obverse and reverse sides in mild weather.

*Lasting quality.*—Very long, a week or more, and drops off cleanly before it begins to dry.

(*g*) Genital organs:

*Stigmas.*—Light Dull Green Yellow (Plate 17) in color; small in size.

*Styles.*—Thin, loosely separated and uneven in height.

*Ovaries.*—Completely enclosed.

*Anthers.*—Medium in size, few in number, Ochraceous Buff (Plate 15) in color, and circular in arrangement.

*Filaments.*—Short and uneven in height, and Sulphur Yellow (Plate 5) in color.

*Pollen.*—Martius Yellow (Plate 4).

(*h*) Foliage:

*Form.*—Compound, with three to five leaflets as a general rule, and occasionally seven.

*Texture.*—Leather on the obverse side, smooth on the reverse side, with ordinary ribs and veins.

*Serrations.*—Sharp and multiple.

*Stipules.*—Medium in length and bearded.

*Color.*—When new or young Victoria Lake (Plate 1) on the upper surface and Oxblood Red (Plate 1) on the under side; and when mature Forest Green (Plate 17) on the upper side or surface and Light Elm Green (Plate 17) on the under surface.

(*i*) Wood:

*Size.*—Medium in diameter, very long in length (ten to fifteen feet when mature).

*Bark.*—Smooth.

*Color.*—Varying shades of brown—the lower or older parts of the canes; Cress Green (Plate 31)—the mature, but not old, canes; Hay's Russet Plate 14)—the younger or newer canes.

(*j*) Thorns:

*Quantity.*—Few.

*Form.*—Short and narrow.

*Color.*—Light Yellowish Olive (Plate 30).

(*k*) Plant: It is a tall growing plant or climber, producing very long canes and branches, that requires supporting structure or trellis to keep it off the ground.

(*l*) Hardiness and disease resistance: It is very resistant to mildew and black-spot infections as observed during growing seasons in Fairport, N. Y., and hardy enough to survive, with light protection of straws or burlap, the average winter season in Fairport, N. Y.

I claim:

A new and distinct variety of rose plant substantially as herein disclosed and described, characterized as to novelty by its similarity to its parent "Demure" (Plant Patent No. 1,065) in respect to its foliage, buds, flowers, colors and fragrance, but distinguished therefrom by its very long shoots or climbing canes which attain such lengths or heights that require a support to keep them off the ground, and which bear flowers on axillary branches extending out at various heights.

No references cited.